(12) United States Patent
Tan et al.

(10) Patent No.: US 11,315,750 B2
(45) Date of Patent: Apr. 26, 2022

(54) ANODE TARGET, RAY LIGHT SOURCE, COMPUTED TOMOGRAPHY SCANNING DEVICE, AND IMAGING METHOD

(71) Applicants: Nuctech Company Limited, Beijing (CN); TSINGHUA UNIVERSITY, Beijing (CN)

(72) Inventors: Chengjun Tan, Beijing (CN); Wenhui Huang, Beijing (CN); Chuanxiang Tang, Beijing (CN); Qingxiu Jin, Beijing (CN); Dongsheng Zhang, Beijing (CN); Qun Luo, Beijing (CN); Donghai Liu, Beijing (CN); Luming Zhang, Beijing (CN); Peidong Wu, Beijing (CN)

(73) Assignees: Nuctech Company Limited, Beijing (CN); TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 16/627,527

(22) PCT Filed: Jun. 1, 2018

(86) PCT No.: PCT/CN2018/089509
§ 371 (c)(1),
(2) Date: Dec. 30, 2019

(87) PCT Pub. No.: WO2019/052232
PCT Pub. Date: Mar. 21, 2019

(65) Prior Publication Data
US 2020/0168426 A1    May 28, 2020

(30) Foreign Application Priority Data

Sep. 18, 2017 (CN) .......................... 201710842782.7
Sep. 18, 2017 (CN) .......................... 201711136934.8

(51) Int. Cl.
*H01J 5/14*    (2006.01)
*H01J 35/14*    (2006.01)
(Continued)

(52) U.S. Cl.
CPC .............. *H01J 35/14* (2013.01); *A61B 6/032* (2013.01); *H01J 35/06* (2013.01); *H01J 35/12* (2013.01);
(Continued)

(58) Field of Classification Search
CPC .. H01J 35/14; H01J 35/06; H01J 35/12; H01J 35/16; H01J 35/153; H01J 2235/068;
(Continued)

(56) References Cited

U.S. PATENT DOCUMENTS 5,438,605 A * 8/1995 Burke ...................... H01J 35/06
378/135
6,125,167 A    9/2000 Morgan
(Continued)

FOREIGN PATENT DOCUMENTS

CN    101346034 A    1/2009
CN    101465260 A    6/2009
(Continued)

OTHER PUBLICATIONS

International Search Report received in International application No. PCT/CN2018/088833, dated Aug. 13, 2018, 4 pages.
(Continued)

*Primary Examiner* — Marcus H Taningco
(74) *Attorney, Agent, or Firm* — Scully Scott Murphy & Presser

(57) ABSTRACT

An anode target comprises: a plurality of target structures, used for receiving an electron beam emitted by a cathode to generate a ray, the plurality of target structures being of three-dimensional structures having bevels; a copper cool-
(Continued)

ing body, used for bearing the target structures and comprising an oxygen-free copper cooling body; a cooling oil tube, used for cooling the anode target; and a shielding layer, used for achieving a shielding effect and comprising a tungsten shielding layer. The anode target, the ray light source, the computed tomography scanning device, and the imaging method in the present application are able to enable all target spots on the anode target to be distributed on a straight line, imaging quality of a ray system is improved, and complexity of an imaging system is reduced.

9 Claims, 9 Drawing Sheets

(51) Int. Cl.
  *H01J 35/06* (2006.01)
  *H01J 35/12* (2006.01)
  *H01J 35/16* (2006.01)
  *A61B 6/03* (2006.01)

(52) U.S. Cl.
  CPC ............ *H01J 35/153* (2019.05); *H01J 35/16* (2013.01); *H01J 2235/068* (2013.01); *H01J 2235/086* (2013.01)

(58) Field of Classification Search
  CPC ........... H01J 2235/086; H01J 2235/166; H01J 2235/1204; H01J 2235/1262; H01J 2235/083; H01J 35/112; H01J 35/08; A61B 6/032; A61B 6/4488; A61B 6/405; A61B 6/4021; A61B 6/482
  See application file for complete search history.

(56) References Cited

U.S. PATENT DOCUMENTS

| | | |
|---|---|---|
| 9,408,577 B2 | 8/2016 | Tamura et al. |
| 2002/0175782 A1 | 11/2002 | Trinh et al. |
| 2003/0072407 A1* | 4/2003 | Mihara .................. H01J 35/112 378/4 |
| 2005/0074094 A1 | 4/2005 | Jen et al. |
| 2005/0084073 A1 | 4/2005 | Seppi et al. |
| 2006/0104418 A1 | 5/2006 | Dunham et al. |
| 2010/0098218 A1 | 4/2010 | Vermilyea et al. |
| 2010/0098219 A1* | 4/2010 | Vermilyea ............... H01J 35/04 378/149 |
| 2010/0111388 A1 | 5/2010 | Seppi et al. |
| 2010/0189223 A1* | 7/2010 | Eaton ...................... H01J 35/16 378/68 |
| 2011/0026680 A1 | 2/2011 | Sato |
| 2011/0176659 A1 | 7/2011 | Rogers et al. |
| 2011/0188625 A1 | 8/2011 | Roshi et al. |
| 2011/0222664 A1 | 9/2011 | Behling |
| 2014/0211924 A1 | 7/2014 | Gerzoskovitz et al. |
| 2015/0078509 A1* | 3/2015 | Tang ....................... H01J 35/02 378/4 |
| 2015/0078510 A1* | 3/2015 | Tang ....................... H01J 35/13 378/9 |
| 2015/0078532 A1* | 3/2015 | Tang ....................... H01J 35/13 378/134 |
| 2015/0250444 A1 | 9/2015 | Tamura |
| 2016/0220207 A1 | 8/2016 | Jouhikainen et al. |
| 2017/0131428 A1 | 5/2017 | Langeveld et al. |
| 2020/0168428 A1* | 5/2020 | Tan ......................... A61B 6/405 |

FOREIGN PATENT DOCUMENTS

| | | |
|---|---|---|
| CN | 102171782 A | 8/2011 |
| CN | 103594308 A | 2/2014 |
| CN | 203563254 U | 4/2014 |
| CN | 203573942 U | 4/2014 |
| CN | 104470172 A | 3/2015 |
| CN | 104882350 A | 9/2015 |
| CN | 107481912 A | 12/2017 |
| CN | 107731644 A | 2/2018 |
| CN | 207909827 U | 9/2018 |
| DE | 10 2012 103 974 A1 | 6/2013 |
| EP | 2 958 127 A1 | 12/2015 |
| JP | H06-215710 A | 8/1994 |
| JP | 2000340149 A | 12/2000 |
| JP | 2009-212010 A | 9/2009 |
| JP | 2011-173778 A | 9/2011 |
| WO | 2014/168589 A1 | 10/2014 |

OTHER PUBLICATIONS

Office Action dated Feb. 8, 2021 received in U.S. Appl. No. 16/627,531.
Behling, R. et al., "Chapter 6: Diagnostic X-Ray Sources from the Inside", Modern Diagnostic X-Ray Sources, Taylor & Francis Group, Jan. 1, 2016, pp. 177-308.
Neculaes, V. B. et al., "Multisource inverse-geometry CT. Part II. X-ray source design and prototype", Medical Physics, Jul. 18, 2016, pp. 4617-4627, vol. 43, No. 8.
Walker, C. A. et al., "Comparing Metal-Ceramic Brazing Methods", Welding Journal, Oct. 1, 2008, pp. 43-50.
Partial Supplementary European Search Report dated May 11, 2021 received in European Patent Application No. EP 18856120.3.
Extended European Search Report dated Jul. 6, 2021 received in European Patent Application No. EP 18856883.6.
Extended European Search Report dated Sep. 24, 2021 received in European Patent Application No. EP 18856120.3.

\* cited by examiner

ANODE TARGET, RAY LIGHT SOURCE, COMPUTED TOMOGRAPHY SCANNING DEVICE, AND IMAGING METHOD

CROSS-REFERENCE TO RELATED APPLICATION

This application is the 371 application of PCT Application No. PCT/CN2018/089509, filed on Jun. 1, 2018, which is based upon and claims priority to Chinese Patent Application No. CN201711136934.8, filed on Sep. 18, 2017 and Chinese Patent Application No. CN201710842782.7, filed on Sep. 18, 2017, the entire contents of all of which are incorporated herein by reference.

TECHNICAL FIELD

X-rays have a wide range of applications in industrial non-destructive testing, safety inspection, medical diagnosis and treatment, and so on. In particular, X-ray fluoroscopic imaging devices utilizing high penetrating capability of X-rays play an important role in every aspect of people's daily life. In the early days, such devices are film-type planar fluoroscopy imaging devices. With the current advanced technologies, they include digital, multi-view and high-resolution stereo imaging devices, such as Computed. Tomography (CT) imaging device, which can obtain three-dimensional graphics or slice images of high-definition, and have become an advanced high-end application. In the existing CT devices, the X-ray generating device needs to move on a slip ring. In order to improve the inspection speed, the movement speed of the X-ray generating device is usually very high, resulting in a decrease in the reliability and stability of the overall device. In addition, the inspection speed of the CT is limited due to the limiting of the movement speed, and as a result, the inspection efficiency is low. In addition, the movement of the X-ray source of such device on the slip ring causes that the focus of the equivalent X-ray light source becomes large, and thus there are motion artifacts in the imaged pictures, the imaged pictures is of poor definition, and there is a possibility of missing detection of some smaller contrabands. Also, such devices can only inspect stationary (or slowly moving) objects, and for the moving objects, it is almost impossible to form a three-dimensional image.

In the prior art, hot cathodes are used as electron-emitting units, and the hot cathodes are arranged in an array. The voltage between the hot cathode and a gate is used to control the emission of electrons, thereby controlling each of the cathodes to emit electrons in sequence so as to bombard target spots on an anode in the respective positions of the sequence, and thus a distributed X-ray source is formed. By replacing the mechanical rotation of the spiral CT with an electronically controlled switch, the X-ray source can be quickly generated from multiple view angles, so that the imaging can be performed rapidly from various angles. Compared with the previous methods, such method can greatly improve the inspection efficiency and the definition of the images, and is of simple structure, system stability and high reliability. However, the existing CT devices can only output a single energy level of high-energy ray beams, which does not satisfy various usage requirements.

Therefore, there is a need for a new anode target, ray light source, computer tomography device, and imaging method.

The information disclosed in Background is only for understanding of the background of the present disclosure, and thus may include information that does not constitute prior art known to those of ordinary skilled in the art.

SUMMARY

In view of the above, the present disclosure provides an anode target, a ray light source, a computer tomography device, and an imaging method, which can provide dual-energy distributed ray imaging data and improve the imaging quality of the ray system.

Other features and advantages of the present disclosure will be apparent from the following detailed description, or acquired in part by the practice of the present disclosure.

According to an aspect of the present disclosure, there is provided an anode target including: a first anode target, configured to cause, by a first voltage bearing thereon, electron beams emitted from cathodes to generate first rays on target spots of the first anode target; a second anode target, configured to cause, by a second voltage bearing thereon, the electron beams emitted from the cathodes to generate second rays on target spots of the second anode target; and a ceramic body, configured to isolate the first anode target from the second anode target.

In an exemplary embodiment of the present disclosure, it further includes: a cooling oil tube, configured to cool the first anode target and the second anode target; and a shielding layer, configured to shield rays generated by the anode targets.

In an exemplary embodiment of the present disclosure, the ceramic body includes a metallized ceramic body.

In an exemplary embodiment of the present disclosure, the first anode target, the second anode target, and the metallized ceramic body are connected by gold-copper welding.

In an exemplary embodiment of the present disclosure, the cathodes are arranged on two sides of the anode targets in a staggered manner.

According to an aspect of the present disclosure, there is provided a ray light source including: cathode assemblies, configured to emit electron beams; and an anode assembly, configured to receive the electron beams from the cathode assemblies and generate a light ray source; wherein the anode assembly includes an anode target, the anode target including: a first anode target, configured to cause, by a first voltage bearing thereon, the electron beams emitted from cathodes to generate first rays on target spots of the first anode target; a second anode target, configured to cause, by a second voltage bearing thereon, the electron beams emitted from the cathodes to generate second rays on target spots of the second anode target; and a ceramic body, configured to isolate the first anode target from the second anode target.

In an exemplary embodiment of the present disclosure, the cathode assemblies are arranged on two sides of the anode targets of the anode assembly in a staggered manner.

According to an aspect of the present disclosure, there is provided a computer tomography device including: cathode assemblies, configured to emit electron beams; and an anode assembly, configured to receive the electron beams from the cathode assemblies and generate a light ray source; wherein the anode assembly includes an anode target, the anode target including: a first anode target, configured to cause, by a first voltage bearing thereon, electron beams emitted from cathodes to generate first rays on target spots of the first anode target; a second anode target, configured to cause, by a second voltage bearing thereon, the electron beams emitted from the cathodes to generate second rays on target spots of the second anode target; and a ceramic body, configured to isolate the first anode target from the second anode target; and an imaging device, configured to perform ray imaging with the first rays and the second rays.

In an exemplary embodiment of the present disclosure, the ray imaging includes dual energy ray imaging.

According to an aspect of the present disclosure, there is provided an imaging method of a computer tomography device including: generating rays by the computed tomography device, the rays including first rays and second rays; applying the first rays to an object for test to generate first test data; applying the second rays to the object for test to generate second test data; and performing ray imaging with the first test data and the second test data; wherein, the computer tomography device includes: cathode assemblies, configured to emit electron beams; and an anode assembly, configured to receive the electron beams from the cathode assemblies and generate a light ray source; wherein the anode assembly includes an anode target, the anode target including: a first anode target, configured to cause, by a first voltage bearing thereon, electron beams emitted from cathodes to generate first rays on target spots of the first anode target; a second anode target, configured to cause, by a second voltage bearing thereon, the electron beams emitted from the cathodes to generate second rays on target spots of the second anode target; and a ceramic body, configured to isolate the first anode target from the second anode target; and an imaging device, configured to perform ray imaging with the first rays and the second rays.

In an exemplary embodiment of the present disclosure, the ray imaging includes dual energy ray imaging.

According to an aspect of the present disclosure, there is provided an anode target including: a plurality of target structures, configured to receive electron beams emitted by cathodes to generate rays, a plurality of target spots being of three-dimensional structures having bevels; a copper cooling body, configured to bear the target structures and include an oxygen-free copper cooling body; a cooling oil tube, configured to cool the anode target; and a shielding layer, configured to achieve a shielding effect and include a tungsten shielding layer.

In an exemplary embodiment of the present disclosure, two adjacent target structures of the plurality of target structures are arranged in a staggered manner.

In an exemplary embodiment of the present disclosure, bevels of two adjacent target structures of the plurality of target structures face towards opposite directions.

In an exemplary embodiment of the present disclosure, target spots of the target structures arranged in a staggered manner are in the same straight line.

In an exemplary embodiment of the present disclosure, the plurality of target structures are weld to the copper cooling body by braze welding.

According to an aspect of the present disclosure, there is provided a ray light source including: cathode assemblies, configured to emit electron beams; and an anode assembly, configured to receive the electron beams from the cathode assemblies and generate a light ray source; wherein the anode assembly includes an anode target, the anode target including: a plurality of target structures, configured to receive electron beams emitted by cathodes to generate rays, the plurality of target structures being of three-dimensional structures having bevels; a copper cooling body, configured to bear the target structures and include an oxygen-free copper cooling body; a cooling oil tube, configured to cool the anode target; and a shielding layer, configured to achieve a shielding effect and include a tungsten shielding layer.

In an exemplary embodiment of the present disclosure, cathodes are arranged on both sides of the anode target in a staggered manner.

In an exemplary embodiment of the present disclosure, two adjacent target structures of the plurality of target structures are arranged in a staggered manner.

In an exemplary embodiment of the present disclosure, target spots of the target structures arranged in a staggered manner are in the same straight line.

According to an aspect of the present disclosure, a computer tomography device is provided, including: cathode assemblies, configured to emit electron beams; and an anode assembly, configured to receive the electron beams from the cathode assemblies and generate a light ray source; wherein the anode assembly includes an anode target, the anode target including: a plurality of target structures, configured to receive electron beams emitted by cathodes to generate rays, the plurality of target structures being of three-dimensional structures having bevels; a copper cooling body, configured to bear the target structures and include an oxygen-free copper cooling body; a cooling oil tube, configured to cool the anode target; and a shielding layer, configured to achieve a shielding effect and include a tungsten shielding layer; and an imaging device, configured to perform ray imaging with the rays.

According to an aspect of the present disclosure, an imaging method of a computer tomography device is provided, including: generating rays by the computed tomography device; applying the rays to an object for test to generate test data; and performing ray imaging directly with the test data; wherein, the computer tomography device includes: cathode assemblies, configured to emit electron beams; and an anode assembly, configured to receive the electron beams from the cathode assemblies and generate a light ray source; wherein the anode assembly includes an anode target, the anode target including: a plurality of target structures, configured to receive electron beams emitted by cathodes to generate rays, the plurality of target structures being of three-dimensional structures having bevels; a copper cooling body, configured to bear the target structures and include an oxygen-free copper cooling body; a cooling oil tube, configured to cool the anode target; and a shielding layer, configured to achieve a shielding effect and include a tungsten shielding layer; and an imaging device, configured to perform ray imaging with the rays.

It should be understood that the above general description and the following detailed description are merely exemplary and are not limiting of the present disclosure.

BRIEF DESCRIPTION OF THE DRAWINGS

The above and other objects, features and advantages of the present disclosure will become more apparent from the detailed description of exemplary embodiments with reference to the drawings. It is apparent that the drawings described below show only some embodiments of the present disclosure, and other drawings can be obtained by those skilled in the art from the drawings described herein without creative effort.

DETAILED DESCRIPTION

Figure 1:
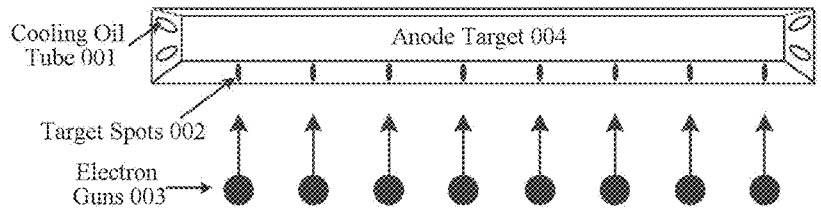
FIG. 1 is a schematic diagram of an anode target arranged in a single line in the prior art.

Exemplary embodiments will now be described more comprehensively with reference to the accompanying drawings. However, the exemplary embodiments can be implemented in a variety of forms and should not be construed as being limited to the embodiments set forth herein; rather, these embodiments are provided so that this disclosure will be more complete and the idea of the exemplary embodiments will be completely conveyed to those skilled in this art. The same reference numerals in the figures denote the same or similar parts, and the repeated description thereof will be omitted.

In addition, the described features, structures, or characteristics can be combined in one or more embodiments in any suitable manner. In the following description, numerous specific details are set forth to provide a thorough understanding of the embodiments of the present disclosure. However, one skilled in the art will appreciate that the technical solutions of the present disclosure can be practiced without one or more of the specific details, or can be practiced with other methods, components, materials, devices, steps, or the like. In other instances, well-known methods, devices, implementations or operations are not shown or described in detail so as to avoid obscuring aspects of the present disclosure.

The block diagrams shown in the figures are only functional entities and do not necessarily correspond to physically or logically separated entities. That is, these functional entities can be implemented in software, implemented in one or more hardware modules or integrated circuits, or implemented in different networks and/or processor devices and/or microcontroller devices.

The flowcharts shown in the figures are merely illustrative, and do not necessarily include all of the contents and operations/steps, and are not necessarily performed in the order described. For example, some of the operations/steps can be decomposed, and some of the operations/steps can be combined or partially combined, and thus the actual execution order may vary depending on the actual situation.

It will be understood that, although the terms of first, second, third, etc. may be used herein to describe various components, these components are not limited by these terms. These terms are used to distinguish one component from another. Accordingly, the first component discussed below can be referred to as a second component without departing from the teaching of the present disclosure. As used herein, the term "and/or" encompasses any and all combinations of one or more of the associated items listed.

Those skilled in the art can understand that the figures are only schematic diagrams of the exemplary embodiments, and the modules or the processes in the figures are not necessarily required to implement the present disclosure, and thus cannot be used to limit the scope of the present disclosure.

The exemplary embodiments of the present disclosure will be described in detail below with reference to the accompanying drawings.

FIG. 1 is a schematic diagram of an anode target arranged in a single line in the prior art.

Figure 2:
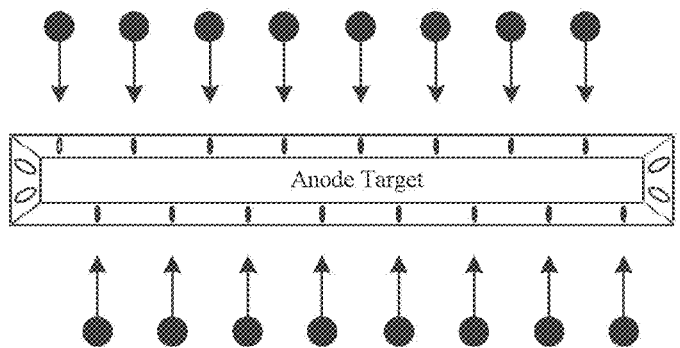
FIG. 2 is a schematic diagram of an anode target arranged in double lines in the prior art.

In the prior art, the anode target arranged in a single row is shown in FIG. 1. FIG. 1 shows a structure of a conventional distributed X-ray light source. The anode target includes oxygen-free copper as a base, and a rhenium-tungsten target welded on the oxygen-free copper as target material. A cooling loop is provided on the oxygen-free copper for cooling the anode target. Electron guns are evenly arranged on one side of the anode target, and the electron beams emitted from the electron guns drift toward the anode under an acceleration of anode electric field, and finally bombard the rhenium-tungsten target to generate X-rays. FIG. 2 is a schematic diagram of anode targets arranged in double lines in the prior art.

In the structure of the CT imaging device in the prior art as described above, in order to improve the imaging quality of the distributed light source, it is generally required that the number of light sources in the distributed light source is from several tens to several hundreds (determined as needed). Affected by the size of the cathode and the processing of the cathode assembly, currently the minimum diameter of the cathode assembly is about 16 mm, and leaving a small margin, the cathode assemblies are usually arranged at a spacing of 20 mm. In a light source with a length of 1 (one) meter, 50 cathode assemblies can be arranged. One cathode assembly produces a target spot on the anode target, thereby forming 50 light sources. If more light sources are needed, the cathodes can be staggered on both sides of the anode targets, and the electron beams emitted by the cathodes strike on both sides of the anode target, thereby doubling the density of the light sources. In order to increase the density of the light sources, the electron guns can be arranged on both sides of the anode targets, as shown in FIG. 2. This structure can double the intensity of the light source to meet the requirements in most occasions.

Figure 3:
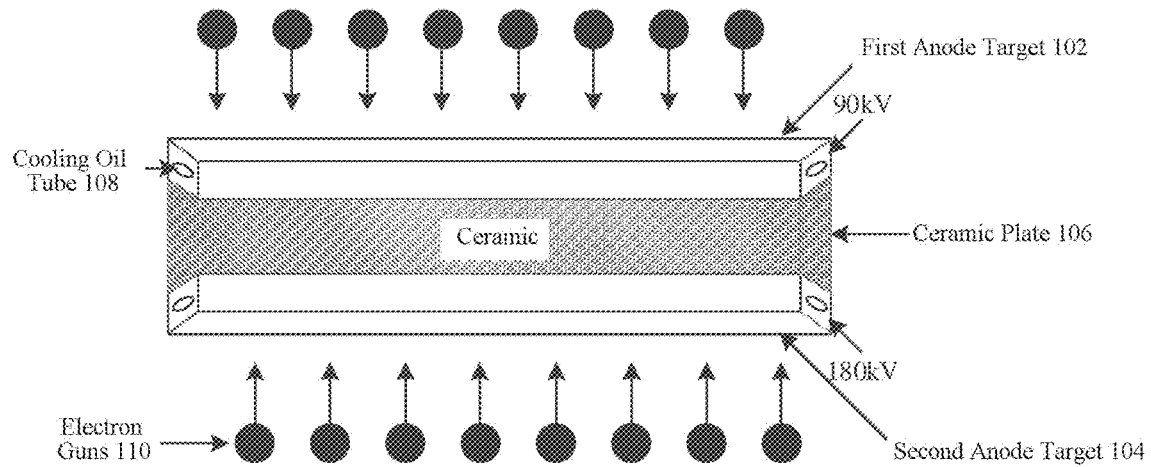
FIG. 3 is a schematic diagram of an anode target according to an exemplary embodiment.

FIG. 3 is a schematic diagram of an anode target according to an exemplary embodiment.

Based on the anode target of the double line arrangement described above, in some embodiments, the applicant of the present application has discovered that, in some cases, there is an requirement for an imaging device to simultaneously output X-ray light sources in two energy levels, i.e., to provide dual energy distributed X-ray light source, so as to improve the resolution of the X-ray imaging system. According to an aspect of the present disclosure, there is proposed an anode target 10 including a first anode target 102, a second anode target 104 and a ceramic body 106.

The first anode target 102 is configured to cause, by a first voltage bearing thereon, electron beams emitted from cathodes to generate first rays on target spots of the first anode target. The first voltage can be a high voltage of, for example, 90 kV, and the first rays generated from the electron beams emitted from the cathodes on the first anode target can be, for example, X-rays having a first energy level.

The second anode target 104 is configured to cause, by a second voltage bearing thereon, the electron beams emitted from the cathodes to generate second rays on target spots of the second anode target. The second voltage can be a high voltage of, for example, 180 kV, and the second rays generated from the electron beams emitted from the cathodes on the second anode target can be, for example, X-rays having a second energy level.

The first voltage and the second voltage can also be high voltages of the same magnitude, and the present disclosure is not limited thereto.

The ceramic body 106 is configured to isolate the first anode target 102 from the second anode target 104. The ceramic body 106 includes a metallized ceramic body. The first anode target 102, the second anode target 104, and the metallized ceramic body are connected by gold-copper welding. The first anode target 102, the second anode target 104, and the metallized ceramic body are gold-copper weld and integrated into one entity, which is convenient for installation and debugging.

In an exemplary embodiment of the present disclosure, it further includes a cooling oil tube 108 configured to cool the first anode target and the second anode target.

A shielding layer (not shown) is configured to shield rays generated by the anode targets.

In an exemplary embodiment of the present disclosure, the cathodes are arranged on two sides of the anode targets in a staggered manner.

According to the anode target of the present disclosure, the anode target is divided into two parts by ceramic isolation, and the anode target parts on the two sides can be respectively applied with different high voltages. Accordingly, the electron beams emitted from the cathodes on the two sides of the anode target bombard on the two sides of the anode targets to generate two types of X-rays with different energy levels, thereby generating dual-energy distributed X-rays, which can provide dual-energy distributed ray imaging data and improve the imaging quality of the ray system.

Figure 4:
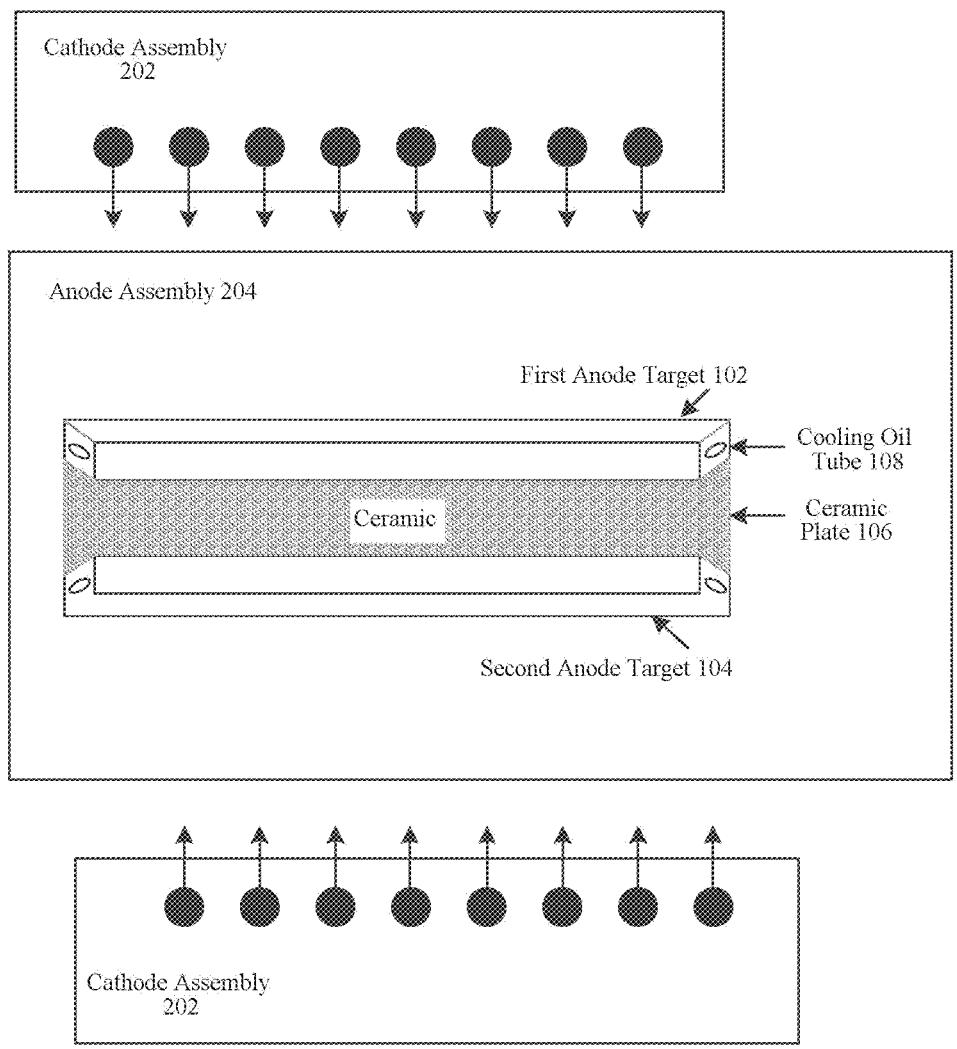
FIG. 4 is a schematic diagram of a ray light source according to an exemplary embodiment.

FIG. 4 is a schematic diagram of a ray light source according to an exemplary embodiment.

As shown in FIG. 4, the ray light source 20 includes cathode assemblies 202 and an anode assembly 204.

The cathode assemblies 202 are configured to emit electron beams which bombard towards the anode assembly 204 by attraction of a voltage.

The anode assembly 204 is configured to receive the electron beams from the cathode assemblies and to form a ray light source by interaction of the electron beam with the anode target.

The anode assembly includes the anode target 10, and the anode target includes a first anode target 102, a second anode target 104 and a ceramic body 106.

The first anode target 102 is configured to cause, by a first voltage, electron beams emitted from cathodes to generate first rays on target spots of the first anode target. The first voltage can be a high voltage of, for example, 90 kV, and the first rays generated by the electron beams emitted from the cathodes on the first anode target can be, for example, X-rays having a first energy level.

The second anode target 104 is configured to cause, by a second voltage, the electron beams emitted from the cathodes to generate second rays on target spots of the second anode target. The second voltage can be a high voltage of, for example, 180 kV, and the second rays generated by the electron beams emitted from the cathodes on the second anode target can be, for example, X-rays having a second energy level.

The first voltage and the second voltage can also be high voltages of the same magnitude, and the present disclosure is not limited thereto.

The ceramic body 106 is configured to isolate the first anode target 102 from the second anode target 104. The ceramic body 106 includes a metallized ceramic body. The first anode target 102, the second anode target 104, and the metallized ceramic body are connected by gold-copper welding. The first anode target 102, the second anode target 104, and the metallized ceramic body are gold-copper weld and integrated into one entity, which is convenient for installation and debugging. In an exemplary embodiment of the present disclosure, the cathode assemblies are arranged on the two sides of the anode targets of the node assembly in a staggered manner.

According to the ray light source of the present disclosure, the electron beams are generated by the cathode assemblies, and are received by the anode assembly. The anode target is divided into two parts by ceramic isolation in the anode assembly, and the anode target parts on the two sides can be respectively applied with different high voltages. Accordingly, the electron beams emitted from the cathodes on the two sides of the anode target bombard on the two sides of the anode target so as to generate two types of X-rays of different energy levels, thereby generating dual-energy distributed X-rays, which can provide the dual-energy distributed ray light source and improve the imaging quality of the ray system.

Figure 5:
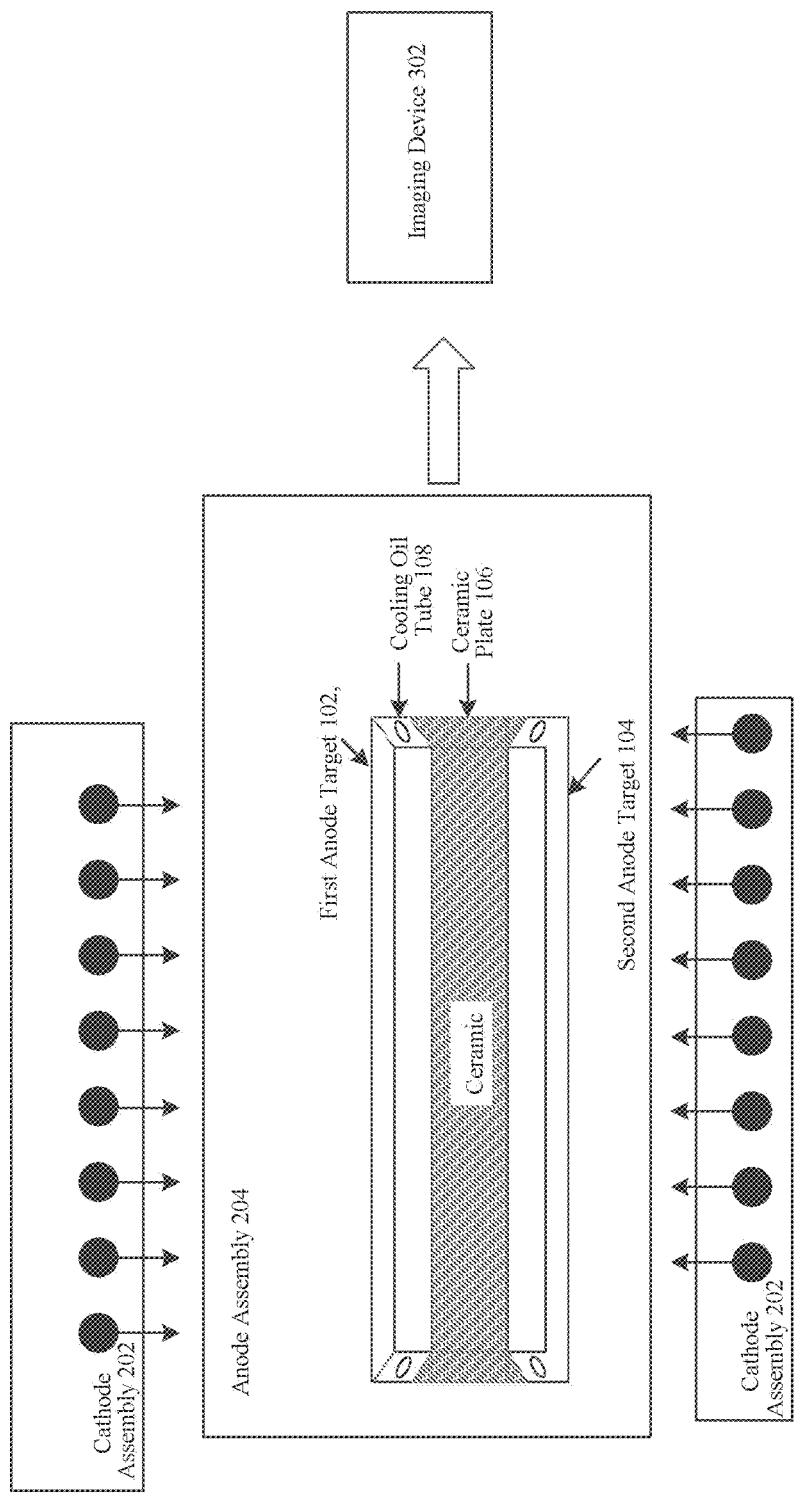
FIG. 5 is a schematic diagram of a computer tomography device according to an exemplary embodiment.

FIG. 5 is a schematic diagram of a computer tomography device according to an exemplary embodiment.

As shown in FIG. 5, the computer tomography device 30 includes cathode assemblies 202, an anode assembly 204 and an imaging device 302.

The cathode assemblies 202 are configured to emit electron beams which bombard towards the anode assembly 204 by attraction of a voltage.

The anode assembly 204 is configured to receive the electron beams from the cathode assemblies and to form a ray light source by interaction of the electron beam with the anode target.

The anode assembly includes an anode target 10, and the anode target includes a first anode target 102, a second anode target 104 and a ceramic body 106.

The first anode target 102 is configured to cause, by a first voltage, electron beams emitted from cathodes to generate first rays on target spots of the first anode target. The first voltage can be a high voltage of, for example, 90 kV, and the first rays generated from the electron beams emitted from the cathodes on the first anode target can be, for example, an X-rays having a first energy level.

The second anode target 104 is configured to cause, by a second voltage bearing thereon, the electron beams emitted from the cathodes to generate second rays on target spots of the second anode target. The second voltage cab be a high voltage of, for example, 180 kV, and the second ray generated from the electron beams emitted from the cathodes on the second anode target can be, for example, X-rays having a second energy level.

The first voltage and the second voltage can also be high voltages of the same magnitude, and the present disclosure is not limited thereto.

The ceramic body 106 is configured to isolate the first anode target 102 from the second anode target 104. The ceramic body 106 includes a metallized ceramic body. The first anode target 102, the second anode target 104, and the metallized ceramic body are connected by gold-copper welding. The first anode target 102, the second anode target 104, and the metallized ceramic body are gold-copper weld and integrated into one entity, which is convenient for installation and debugging. In an exemplary embodiment of the present disclosure, the cathode assemblies are arranged on the two sides of the anode targets of the node assembly in a staggered manner.

The imaging device 302 is configured to perform ray imaging with the first rays and the second rays. The ray imaging performed by the imaging device includes dual energy ray imaging.

According to the computer tomography device of the present disclosure, the electron beams are generated by the cathode assemblies, and are received by the anode assembly. The anode target is divided into two parts by ceramic isolation in the anode assembly, and the anode target parts on the two sides can be respectively applied with different high voltages. Accordingly, the electron beams emitted from the cathodes on the two sides of the anode target bombard on the two sides of the anode target so as to generate two types of X-rays of different energy levels, thereby generating dual-energy distributed X-rays. The imaging device performs the ray imaging by using the dual energy distributed X-rays, which can provide the dual-energy ray imaging and improve the imaging quality of the ray system.

It will be clearly understood that the present disclosure describes how to make and use particular examples, but the principles of the present disclosure are not limited to the details of the examples. Rather, these principles can be applied to many other embodiments based on the teaching of the present disclosure.

Figure 6:
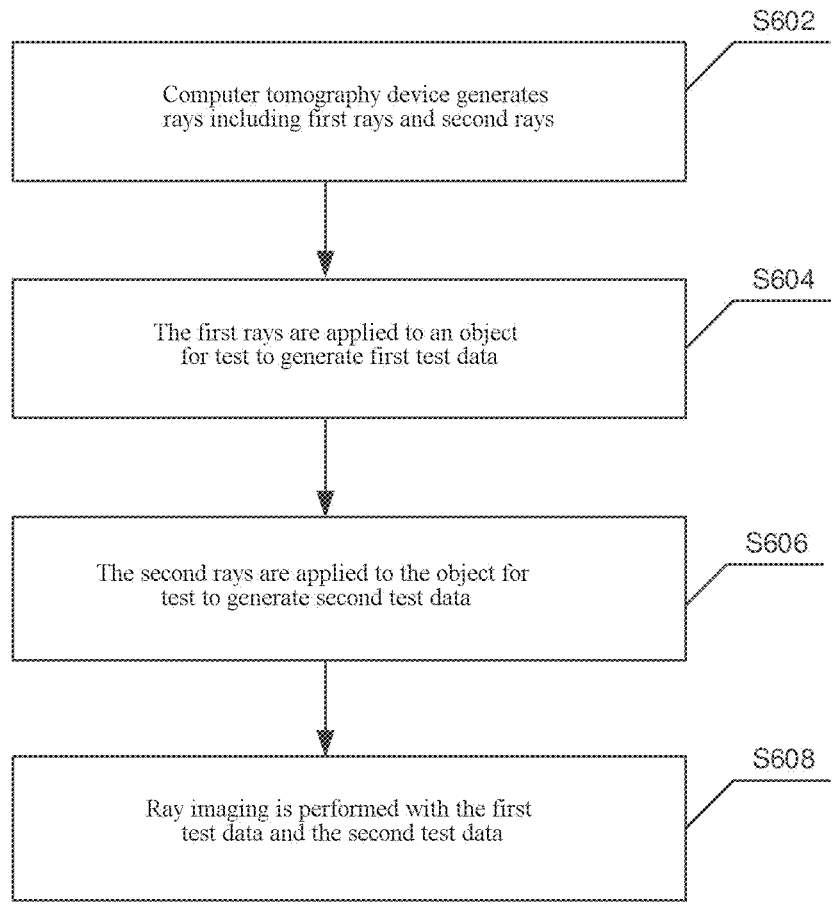
FIG. 6 is a flowchart of an imaging method of a computer tomography device according to an exemplary embodiment.

FIG. 6 is a flowchart of an imaging method of a computer tomography device according to an exemplary embodiment.

In S602, the computer tomography device generates rays including first rays and second rays. The computer tomography device includes: cathode assemblies, configured to emit electron beams; and an anode assembly, configured to receive the electron beams from the cathode assemblies and to form a light ray source. The anode assembly includes an anode target including: a first anode target, configured to cause, by a first voltage, electron beams emitted from cathodes to generate first rays on target spots of the first anode target; a second anode target, configured to cause, by a second voltage bearing thereon, the electron beams emitted from the cathodes to generate second rays on target spots of the second anode target; and a ceramic body, configured to isolate the first anode target from the second anode target.

In S604, the first rays are applied to an object for test so as to generate first test data.

In S606, the second rays are applied to an object for test so as to generate second test data.

In S608, ray imaging is performed with the first test data and the second test data. The imaging can be performed by for example, an imaging device in the computer tomography device, or by for example, other imaging devices, which is not limited by the present disclosure. The ray imaging includes dual energy ray imaging. An imaging calculation can be performed, for example, by the dual energy imaging methods in the prior art, and the present disclosure is not limited thereto.

Those skilled in the art will appreciate that all or part of the steps for implementing the above-described embodiments are implemented as a computer program executed by a CPU. The computer program, when executed by the CPU, performs the above-described functions defined by the above-described methods provided in the present disclosure. The program can be stored in a computer readable storage medium, which can be a read only memory, a magnetic disk, an optical disk or the like.

Further, it should be noted that the above-described drawings are merely illustration of the processes included in the methods according to the exemplary embodiments of the present disclosure, and are not intended to be limiting. It is easy to understand that the processes shown in the above figures does not indicate or limit the temporal order of these processes. In addition, it is also easy to understand that these processes may be performed synchronously or asynchronously, for example, in a plurality of modules.

It will be understood by those skilled in the art that the above various modules can be distributed in a device according to the description of the embodiments, or can be distributed in one or more devices different from the embodiments by making corresponding change. The modules in the above embodiments can be combined into one module or can be further divided into a plurality of sub-modules.

Through the description of the above embodiments, those skilled in the art will readily understand that the exemplary embodiments described herein may be implemented in software or in a combination of software with necessary hardware components. Therefore, the technical solutions according to embodiments of the present disclosure can be embodied in the form of a software product, which can be stored in a non-volatile storage medium (which can be a CD-ROM, a USB flash drive, a mobile hard disk, etc.) or on a network. It includes a number of pieces of instructions to cause a computing device (which can be a personal computer, a server, a mobile terminal, a network device, or the like.) to perform the methods in accordance with the embodiments of the present disclosure.

From the above detailed description, those skilled in the art will readily appreciate that the anode target, the ray light source, the computer tomography device, and the imaging method according to embodiments of the present disclosure have one or more of the following advantages.

According to some embodiments, the anode target of the present disclosure is divided into two parts by ceramic isolation, and the anode target parts on the two sides can be respectively applied with different high voltages. Accordingly, the electron beams emitted from the cathodes on the two sides of the anode target bombard on the two sides of the anode target so as to generate two types of X-rays of different energy levels, thereby generating dual-energy distributed X-rays, which can provide dual-energy distributed ray imaging data and improve the imaging quality of the ray system.

According to some other embodiments, in the computer tomography device of the present disclosure, the electron beams are generated by the cathode assemblies, and are received by the anode assembly, the raying imaging is performed by the imaging device, thereby providing the dual-energy ray imaging data and improving the imaging quality of the ray system.

Figure 7:
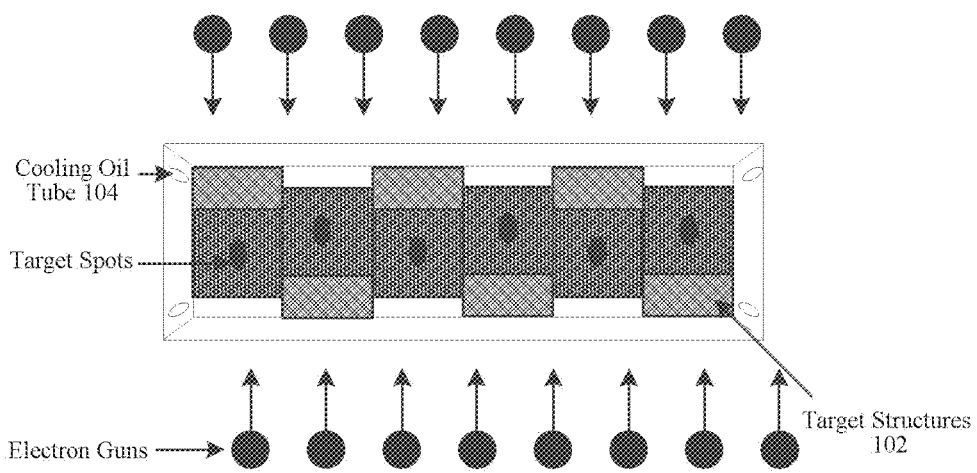
FIG. 7 is a schematic diagram of an anode target according to an exemplary embodiment.

FIG. 7 is a schematic diagram of an anode target according to an exemplary embodiment.

Based on the anode target of the double line arrangement described above, according to an aspect of the present disclosure, there is provided an anode target 1000 including a plurality of target structures 102 and a cooling oil tube 104.

The plurality of target structures 102 are configured to receive electron beams emitted by cathodes so as to generate rays. The plurality of target structures are of three-dimensional structures having bevels. Two adjacent ones of the plurality of target structures are arranged in a staggered manner. Bevels of two adjacent ones of the plurality of target structures 102 face towards opposite directions. Target spots of the staggered target structures 102 are in the same straight line. The target structures can be, for example, rhenium tungsten targets. The target structures 102 are configured to carry high voltages that cause the electron beams to generate the rays at the target spots of the target structures 102. The high voltage can be, for example, a high voltage of 90 kV, or can also be, for example, a high voltage of 180 kV, and the present disclosure is not limited thereto. The rays generated by the target structures 102 can be, for example, X-rays, and the generated X-rays have different energy levels corresponding to different high voltages, and the present disclosure is not limited thereto.

A copper cooling body (not shown) is configured to bear the target structures and includes an oxygen-free copper cooling body. The plurality of target structures 102 can be weld to the copper cooling body by braze welding, for example. The target structures 102 can be weld to the copper cooling body, for example, at the back sides or the bottom sides by one-time welding. A cooling body and a heat-conducting body of the oxygen-free copper transfer heat deposited on the target material to a cooling medium to be taken away.

The cooling oil tube 104 is configured to cool the anode target.

A shielding layer (not shown) is configured to achieve a shielding effect and includes a tungsten shielding layer. The tungsten shielding layer is fixed in an incident direction of the electron beams, for reducing the electric field gradient on the surface of the anode target on the one hand and for shielding the X-rays exiting from the anode target and ensuring that the X-rays only exit right upward and that the X-ray doses in other directions are as small as possible on the other hand, which reduces the difficulty of shielding the radiation from the entire ray light source.

The electron beams are accelerated by the high voltage of the anode, pass through the tungsten shielding layer, and bombard on the rhenium tungsten target so as to generate the X-rays.

Figure 8:
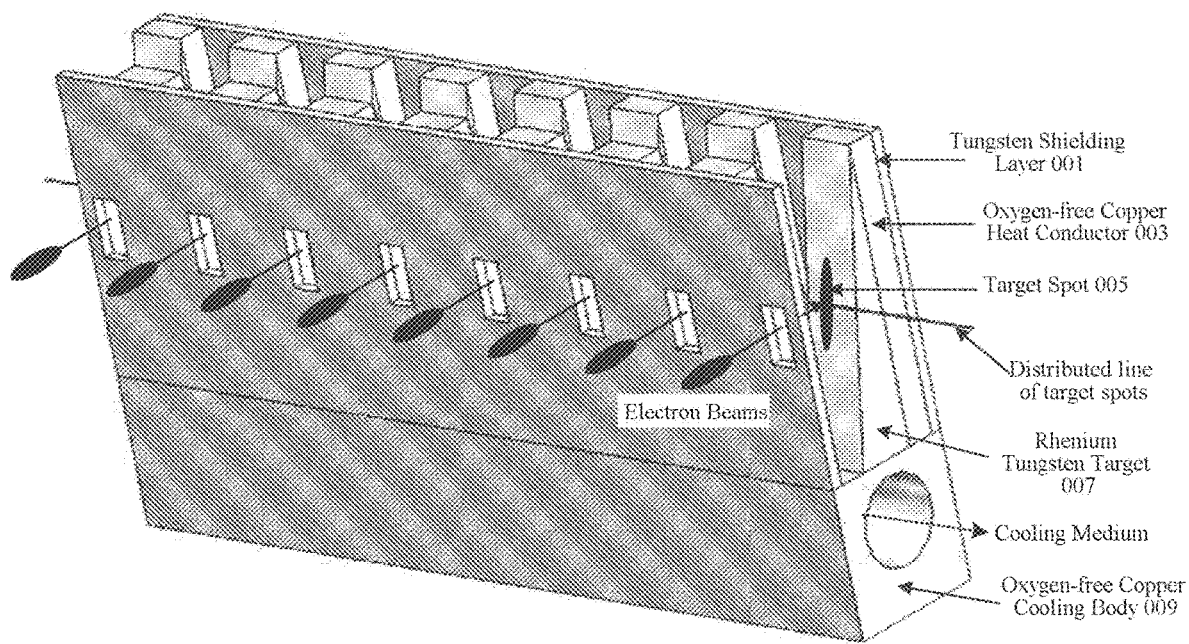
FIG. 8 is a schematic diagram of a side view of an anode target according to an exemplary embodiment.
Figure 9:
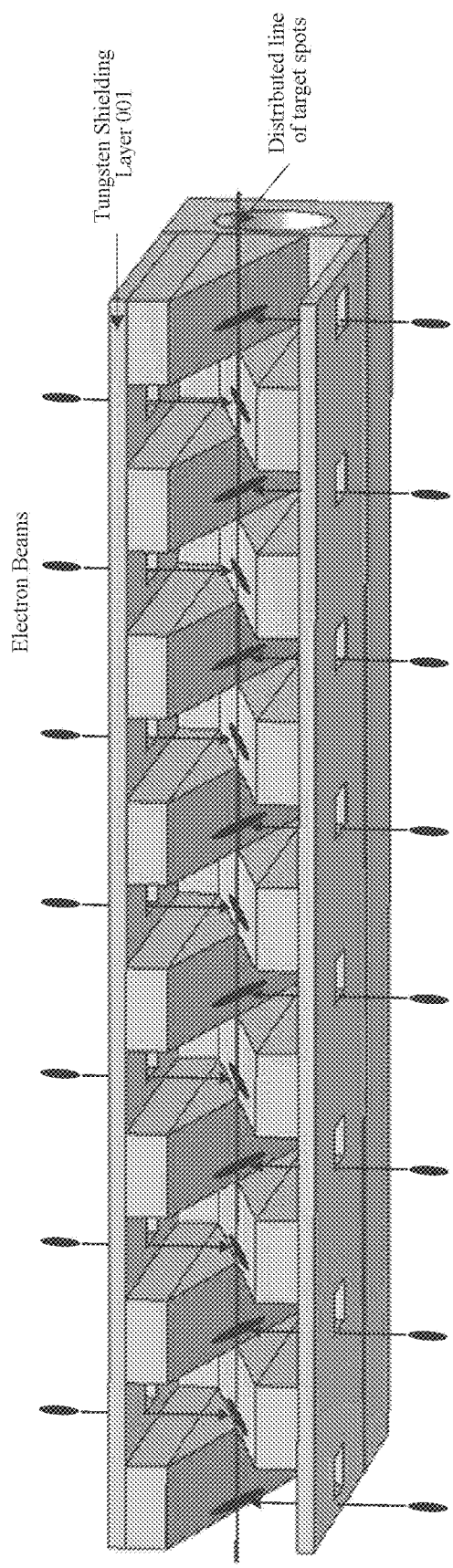
FIG. 9 is a top view of an anode target according to an exemplary embodiment.

FIG. 8 is a schematic diagram of a side view of an anode target according to an exemplary embodiment, and FIG. 9 is a top view of an anode target according to an exemplary embodiment. As can be seen, the two adjacent rhenium tungsten targets 102 are arranged in a staggered manner, and the slopes of the two adjacent rhenium tungsten targets 102 face towards opposite directions so as to receive the electrons emitted from the electron guns on both sides of the anode targets. The centers of the two anode targets 102 which are arranged in a staggered manner are in a straight line, and the positions in which the electron beams bombard the anode targets are also the center positions of the anode targets 102, so that a distributed X-ray light source having focuses in a straight line can be generated. Such method allows that when the electron guns are arranged on both sides of the anode targets, the resulting target spots are also in the same line.

According to the anode target of the present disclosure, with the target structures having the three-dimensional structures with bevels and arranged in a staggered manner, it is enabled that the target spots of the electrons emitted from the cathodes arranged on both sides of the anode targets which bombard on the anode targets are all distributed in a straight line, so that when the electron guns are arranged on both sides of the anode targets, the resulting target spots are also in the same line, thereby improving the imaging quality of the ray system, and simplifying the complexity of the imaging system.

Figure 10:
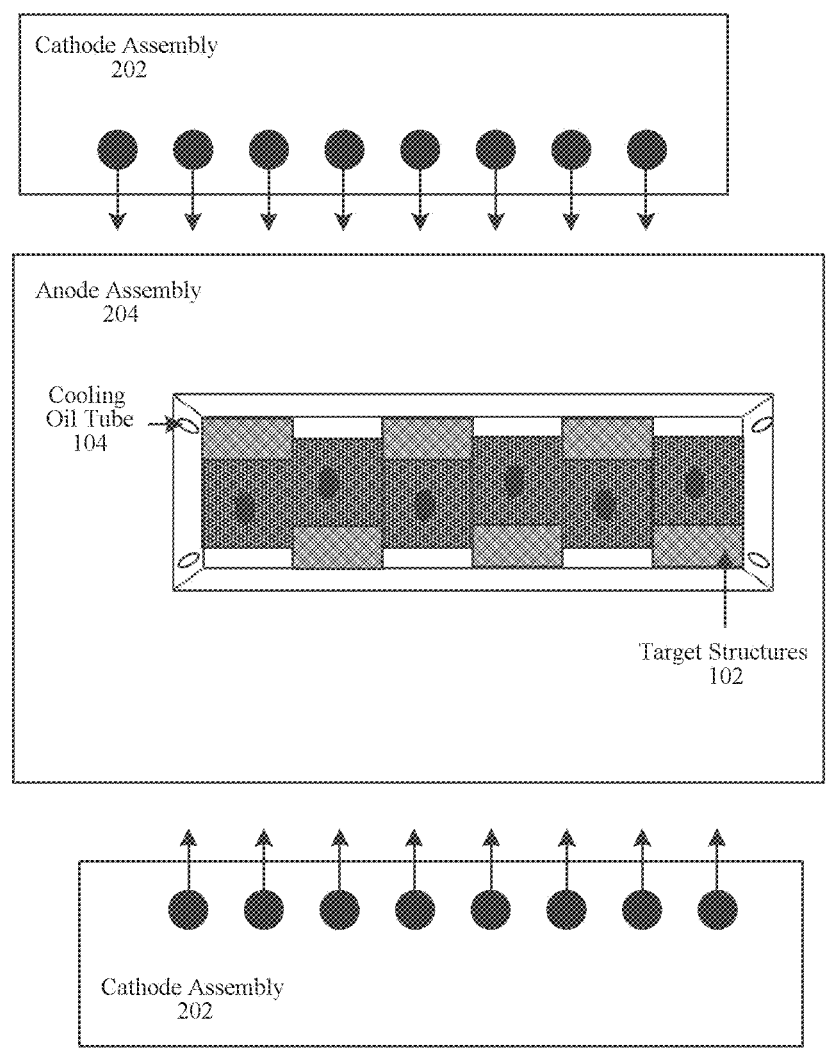
FIG. 10 is a schematic diagram of a ray light source according to an exemplary embodiment.

FIG. 10 is a schematic diagram of a ray light source according to an exemplary embodiment.

As shown in FIG. 10, the ray light source 2000 includes cathode assemblies 202 configured to emit electron beams which are shot towards an anode assembly 204 by attraction of a voltage.

The anode assembly 204 is configured to receive the electron beams from the cathode assemblies so as to generate a ray light source by interaction of the electron beams with an anode target.

The anode assembly includes an anode target 1000, and the anode target includes a plurality of target structures 102 and a cooling oil tube 104.

The plurality of target structures 102 are configured to receive electron beams emitted by cathodes so as to generate rays. The plurality of target spots are of three-dimensional structures having bevels. Two adjacent ones of the plurality of target structures are arranged in a staggered manner. Bevels of two adjacent ones of the plurality of target structures 102 face towards opposite directions. Target spots of the staggered target structures 102 are in the same straight line. The target structures can be, for example, rhenium tungsten targets. The target structures 102 are configured to carry high voltages that cause the electron beams to generate the rays at the target spots of the target structures 102. The high voltage can be, for example, a high voltage of 90 kV, or can be, for example, a high voltage of 180 kV, and the present disclosure is not limited thereto. The rays generated by the target structures 102 can be, for example, an X-ray, and the generated X-rays have different energy levels corresponding to different high voltages, and the present disclosure is not limited thereto.

A copper cooling body (not shown) is configured to bear the target structures and includes an oxygen-free copper cooling body. The plurality of target structures 102 can be weld to the copper cooling body by braze welding, for example. The target structures 102 can be weld to the copper cooling body, for example, at the back sides or the bottom sides by one-time welding. A cooling body and a heat conducting body of the oxygen-free copper transfer heat deposited on the target material to a cooling medium to be taken away.

The cooling oil tube 104 is configured to cool the anode target.

A shielding layer (not shown) is configured to achieve a shielding effect and includes a tungsten shielding layer. The tungsten shielding layer is fixed in an incident direction of the electron beam, for reducing the electric field gradient on the surface of the anode target on the one hand, and for shielding the X-rays exiting from the anode target and ensuring that the X-rays only exit right upward, and that the X-ray doses in other directions are as small as possible on the other hand, which reduces the difficulty of shielding the radiation from the entire ray light source.

According to the ray light source of the present disclosure, the electron beams are generated by the cathode assemblies, and tare received by the anode assembly, and with the target structures having the three-dimensional structures with bevels and arranged in a staggered manner, it is enabled that all the target spots on the anode target are distributed in a straight line, so that when the electron guns are arranged on both sides of the anode targets, the resulting target spots are also in the same line, thereby improving the imaging quality of the ray system, and simplifying the complexity of the imaging system.

Figure 11:
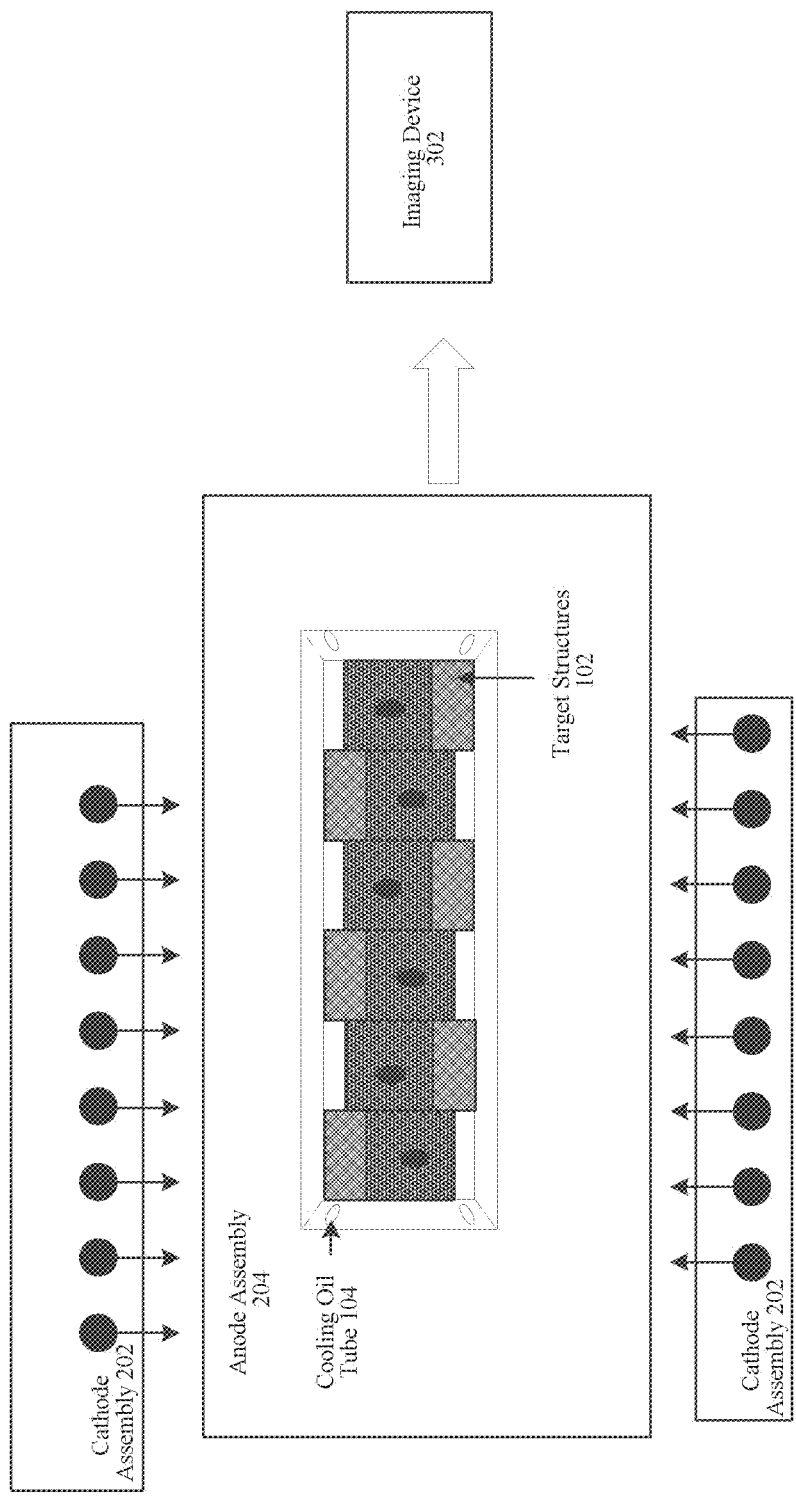
FIG. 11 is a schematic diagram of a computer tomography device according to an exemplary embodiment.

FIG. 11 is a schematic diagram of a computer tomography device according to an exemplary embodiment.

As shown in FIG. 11, the computer tomography device 3000 includes cathode assemblies 202, an anode assembly 204, and an imaging device 302.

The cathode assemblies 202 are configured to emit electron beams which are shot towards the anode assembly 204 by attraction of a voltage.

The anode assembly 204 is configured to receive the electron beams from the cathode assemblies so as to generate a ray light source by interaction of the electron beam with an anode target.

The anode assembly includes an anode target 1000, and the anode target includes a plurality of target structures 102 and a cooling oil tube 104.

The plurality of target structures 102 are configured to receive electron beams emitted by cathodes so as to generate rays. A plurality of target spots are of three-dimensional structures having bevels. Two adjacent ones of the plurality of target structures are arranged in a staggered manner. Bevels of two adjacent ones of the plurality of target structures 102 face towards opposite directions. Target spots of the staggered target structures 102 in the same straight line. The target structures can be, for example, rhenium tungsten targets. The target structures 102 are configured to carry high voltages that cause the electron beams to generate the rays at the target spots of the target structures 102. The high voltage can be, for example, a high voltage of 90 kV, or can be, for example, a high voltage of 180 kV, and the present disclosure is not limited thereto. The rays generated by the target structures 102 can be, for example, X-rays, and the generated X-rays have different energy levels corresponding to different high voltages, and the present disclosure is not limited thereto.

A copper cooling body (not shown) is configured to bear target structures and includes an oxygen-free copper cooling body. The plurality of target structures 102 can be weld to the copper cooling body by braze welding, for example. The target structures 102 can be weld to the copper cooling body, for example, at the back sides or the bottom sides by one-time welding. A cooling body and a heat conducting body of the oxygen-free copper transfer heat deposited on the target material to a cooling medium to be taken way.

The cooling oil tube 104 is configured to cool the anode target.

A shielding layer (not shown) is configured to achieve a shielding effect and includes a tungsten shielding layer. The tungsten shielding layer is fixed in an incident direction of the electron beams, for reducing the electric field gradient on the surface of the anode target on the one hand and for shielding the X-rays exiting from the anode target and ensuring that the X-rays only exit righty upward and that the X-ray doses in other directions are as small as possible on the other hand, which reduces the difficulty of shielding the radiation from the entire ray light source.

The imaging device 302 is configured to perform ray imaging with the first rays and the second rays. The ray imaging performed by the imaging device includes dual energy ray imaging.

According to the computer tomography device of the present disclosure, the electron beams are generated by the cathode assemblies, and are received by the anode assembly, and with the target structures having the three-dimensional structures with bevels and arranged in a staggered manner, it is enabled that all the target spots on the anode targets are distributed in a straight line, so that when the electron guns are arranged on both sides of the anode targets, the resulting target spots are also in the same line, and then the ray imaging is performed by the imaging device, thereby improving the imaging quality of the ray system, and simplifying the complexity of the imaging system.

It will be clearly understood that the present disclosure describes how to make and use particular examples, but the principles of the present disclosure are not limited to the details of the examples. Rather, these principles can be applied to many other embodiments based on the teachings of the present disclosure.

Figure 12:
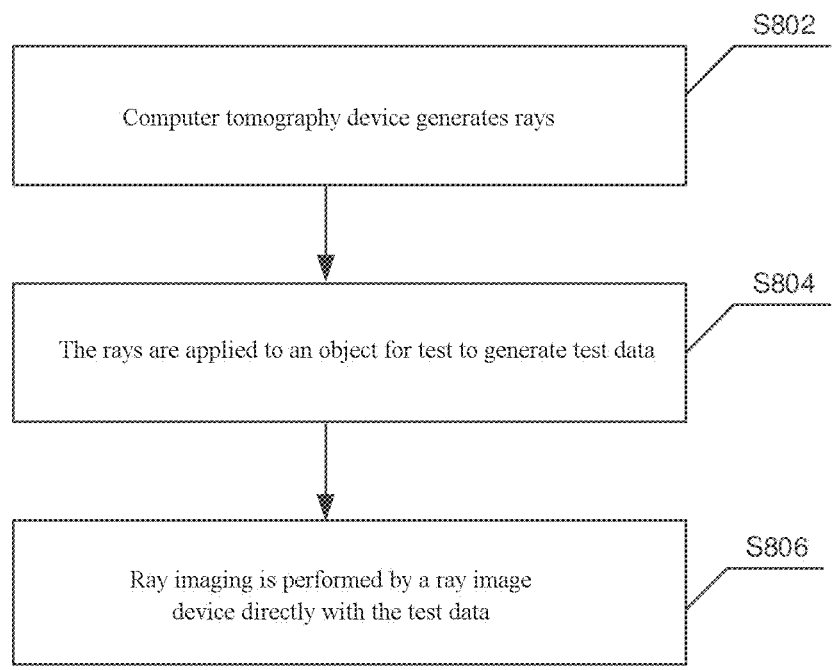
FIG. 12 is a flowchart of an imaging method of a computer tomography device according to an exemplary embodiment.

FIG. 12 is a flowchart of an imaging method of a computer tomography device according to an exemplary embodiment.

In S802, the computer tomography device generates rays. The computer tomography device includes: cathode assemblies, configured to emit electron beams; and an anode assembly, configured to receive the electron beams from the cathode assemblies and generate a ray light source. The anode assembly includes an anode target, the anode target including: a plurality of target structures, configured to receive electron beams emitted by cathodes to generate a rays, the plurality of target structures being of three-dimensional structures having bevels; a copper cooling body, configured to bear the target structures and include an oxygen-free copper cooling body; a cooling oil tube, configured to cool the anode target; and a shielding layer, configured to achieve a shielding effect and include a tungsten shielding layer.

In S804, the rays are applied to an object for test to generate test data.

In S806, a ray imaging is performed by a ray imaging device directly with the test data. The imaging can be performed by for example, an imaging device in the computer tomography device, or by for example, other imaging devices, which is not limited by the present disclosure.

Those skilled in the art will appreciate that all or a portion of the steps for implementing the above-described embodiments are implemented as a computer program executed by a CPU. The computer program, when being executed by the CPU, performs the above-described functions defined by the above-described methods provided by the present disclosure. The program can be stored in a computer readable storage medium which can be a read only memory, a magnetic disk, an optical disk or the like.

Further, it should be noted that the above-described drawings are merely illustrative of the processes included in the methods according to the exemplary embodiments of the present disclosure, and are not intended to be limiting. It is easy to understand that the processes shown in the above figures do not indicate or limit the temporal order of these processes. In addition, it is also easy to understand that these processes can be performed synchronously or asynchronously, for example, in a plurality of modules.

It will be understood by those skilled in the art that the above various modules can be distributed in a device according to the description of the embodiments, or can be distributed in one or more devices different from the embodiments by making corresponding change. The modules in the above embodiments can be combined into one module or can be further divided into a plurality of sub-modules.

Through the description of the above embodiments, those skilled in the art will readily understand that the exemplary embodiments described herein can be implemented by software or by a combination of software with necessary hardware components. Therefore, the technical solutions according to embodiments of the present disclosure can be embodied in the form of a software product, which can be stored in a non-volatile storage medium (which can be a CD-ROM, a USB flash drive, a mobile hard disk, etc.) or on a network. A number of pieces of instructions are included to cause a computing device (which can be a personal computer, server, mobile terminal, or network device, etc.) to perform the methods in accordance with the embodiments of the present disclosure.

From the above detailed description, those skilled in the art will readily appreciate that the anode target, the ray light source, the computer tomography device, and the imaging method according to embodiments of the present disclosure have one or more of the following advantages.

According to some embodiments, with the target structures having the three-dimensional structures with bevels and arranged in a staggered manner, the anode target of the present disclosure enables that the target spots on the anode target are all distributed in a straight line, so that when the electron guns are arranged on both sides of the anode target, the resulting target spots are also in the same line, thereby improving the imaging quality of the ray system, and simplifying the complexity of the imaging system.

According to some other embodiments, the ray light source of the present disclosure generates the electron beams by the cathode assemblies, and receives the electron beams by the anode assembly, and with the target structures having the three-dimensional structures with bevels and arranged in a staggered manner, it is enabled that the target spots on the anode target are all distributed in a straight line, so that when the electron guns are arranged on both sides of the anode target, the resulting target spots are also in the same line, thereby improving the imaging quality of the ray system, and simplifying the complexity of the imaging system.

According to still further embodiments, the computer tomography device of the present disclosure generates the electron beams by the cathode assemblies, and receives the electron beams by the anode assembly, and with the target structures having the three-dimensional structures with bevels and arranged in a staggered manner, it is enabled that all the target spots on the anode targets are distributed in a straight line, so that when the electron guns are arranged on both sides of the anode target, the resulting target spots are also in the same line, and then the ray imaging is performed by the imaging device, thereby improving the imaging quality of the ray system, and simplifying the complexity of the imaging system.

The anode target structure of the present disclosure can double the intensity of the light sources and improve the imaging quality of the system.

According to the anode target, the ray light source, the computer tomography device, and the imaging method of the present disclosure, it is possible to provide dual energy ray imaging data, thereby improving the imaging quality of the ray system.

The present disclosure also provides a anode target, a ray light source, a computer tomography device, and an imaging method, so that the target spots on which the X-rays emitted from the cathodes arranged on both sides of the anode targets bombard the anode target are all distributed in a straight line, thereby improving the intensity of the light sources, improving the imaging quality of the ray system, and simplifying the complexity of the imaging system.

Other features and advantages of the present disclosure will be apparent from the following detailed description, or learned in part by the practice of the present disclosure.

The anode target, the distributed X-ray light source, the computer tomography device and the imaging method according to the present disclosure enable the target spots on which the electrons emitted from the cathodes arranged on both sides of the anode targets bombard the anode target are all distributed in a straight line, thereby improving the imaging quality of the ray system, and simplifying the complexity of the imaging system.

The exemplary embodiments of the present disclosure have been particularly shown and described above. It is to be understood that the present disclosure is not limited to the detailed structures, arrangements, or implementations described herein; rather, the present disclosure is intended to cover various modifications and equivalent arrangements within the spirit and scope of the appended claims.

In addition, the structures, the proportions, the sizes, and the like shown in the drawings of the present specification are only used to work in with the contents disclosed in the specification, can be understood and read by those skilled in the art, and are not intended to limit the conditions in which the present disclosure can be implemented and thus it does not have any technical significance. Any modification to the structures, change in the proportional relationship or adjustment of the size, without affecting the technical effects and the objectives that can be achieved in the present disclosure, should still fall within the scope that can be covered by the technical content disclosed in the present disclosure. In the meantime, the terms, such as "upper", "first", "second", "a", "an" and so on referred to in the description are also for the convenience of description, and are not intended to limit the scope of the disclosure. The change or adjustment of the relative relationship is also considered to be in the scope in which the present disclosure can be implemented without substantial changes in the technical content.

What is claimed is:

1. An anode target, comprising:
    a plurality of target structures, configured to receive electron beams emitted by cathodes to generate rays, the plurality of target structures being of three-dimensional structures having bevels, the bevels of every two adjacent target structures of the plurality of target structures facing towards opposite directions to receive electron beams emitted by the cathodes on two sides of the target structures, wherein every two adjacent target structures of the plurality of target structures are arranged in a staggered manner, and target spots on the bevels of the plurality of target structures arranged in a staggered manner are in the same straight line;
    a copper cooling body, configured to bear the target structures and including an oxygen-free copper cooling body;
    a cooling oil tube, configured to cool the anode target; and
    a shielding layer, configured to achieve a shielding effect and including a tungsten shielding layer.

2. The anode target of claim 1, wherein material of the target structures includes rhenium-tungsten material.

3. The anode target of claim 1, wherein the plurality of target structures are weld to the copper cooling body by braze welding.

4. A ray light source, comprising:
    cathode assemblies, configured to emit electron beams; and
    an anode assembly, configured to receive the electron beams from the cathode assemblies and generate a ray light source;
    wherein the anode assembly includes an anode target, and the anode target includes:
    a plurality of target structures, configured to receive the electron beams emitted by cathode assemblies to generate rays, the plurality of target structures being of three-dimensional structures having bevels, the bevels of every two adjacent target structures of the plurality of target structures facing towards opposite directions to receive electron beams emitted by the cathodes on two sides of the target structures, wherein every two adjacent target structures of the plurality of target structures are arranged in a staggered manner, and target spots on the bevels of the plurality of target structures arranged in a staggered manner are in the same straight line;

a copper cooling body, configured to bear the target structures and including an oxygen-free copper cooling body;

a cooling oil tube, configured to cool the anode target; and a shielding layer, configured to achieve a shielding effect and including a tungsten shielding layer.

5. The ray light source of claim 4, wherein the number of the cathode assemblies are equal to or more than two, and the two or more cathode assemblies are arranged on both sides of the anode target in a staggered manner.

6. A computer tomography device, comprising:

cathode assemblies, configured to emit electron beams;

an anode assembly, configured to receive the electron beams from the cathode assemblies and generate a ray light source, wherein the anode assembly includes an anode target, the anode target including:

a plurality of target structures, configured to receive the electron beams emitted by the cathode assembly to generate rays, the plurality of target structures being of three-dimensional structures having bevels, the bevels of every two adjacent target structures of the plurality of target structures facing towards opposite directions to receive electron beams emitted by the cathode assemblies on two sides of the target structures, wherein every two adjacent target structures of the plurality of target structures are arranged in a staggered manner, and target spots on the bevels of the plurality of target structures arranged in a staggered manner are in the same straight line;

a copper cooling body, configured to bear the target structures and including an oxygen-free copper cooling body;

a cooling oil tube, configured to cool the anode target; and a shielding layer, configured to achieve a shielding effect and including a tungsten shielding layer; and an imaging device, configured to perform ray imaging with the rays.

7. The computer tomography device of claim 6, wherein the number of the cathode assemblies are equal to or more than two, and the two or more cathode assemblies are arranged on both sides of the anode target in a staggered manner.

8. The computer tomography device of claim 6, wherein material of the target structures includes rhenium-tungsten material.

9. The computer tomography device of claim 6, wherein the plurality of target structures are weld to the copper cooling body by braze welding.

* * * * *